United States Patent
Fukuda (10) Patent No.: US 10,779,784 B2
(45) Date of Patent: Sep. 22, 2020

(54) MAMMARY GLAND AMOUNT ACQUISITION APPARATUS, METHOD, AND PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 196 days.

(21) Appl. No.: 15/922,858

(22) Filed: Mar. 15, 2018

(65) Prior Publication Data
US 2018/0279982 A1  Oct. 4, 2018

(30) Foreign Application Priority Data
Mar. 29, 2017 (JP) .................... 2017-065097

(51) Int. Cl.
*A61B 6/00* (2006.01)
*A61B 5/00* (2006.01)
(Continued)

(52) U.S. Cl.
CPC ........... *A61B 6/502* (2013.01); *A61B 5/1072* (2013.01); *A61B 5/4312* (2013.01);
(Continued)

(58) Field of Classification Search
CPC ..... A61B 6/502; A61B 5/1072; A61B 5/4312; A61B 5/4872; A61B 5/5217; A61B 5/1073; A61B 6/0414; G06T 7/0014; G06T 2207/10116; G06T 2207/20021; G06T 2207/30068
(Continued)

(56) References Cited

U.S. PATENT DOCUMENTS 5,595,177 A * 1/1997 Mena .................. A61B 6/0414
                                                         303/130
8,340,380 B2   12/2012 Morita
(Continued)

FOREIGN PATENT DOCUMENTS

JP  2009247521   10/2009
JP  2010-253245  11/2010
(Continued)

OTHER PUBLICATIONS

"Office Action of Japan Counterpart Application," with machine English translation thereof, dated Jan. 7, 2020, p. 1-p. 7.

*Primary Examiner* — Blake C Riddick
(74) *Attorney, Agent, or Firm* — JCIPRNET (57) ABSTRACT

A subject information acquisition unit of a mammary gland amount calculation unit acquires the thickness and the mammary gland amount of the breast based on a low voltage image. An absorption coefficient acquisition unit acquires an absorption coefficient of fat and an absorption coefficient of mammary gland with reference to the relationship between the thickness of the breast and the X-ray absorption coefficient, which is calculated in advance according to the energy distribution and the substance forming the breast. A calculation unit calculates a new thickness and a new mammary gland amount of the breast based on the low voltage image, a high voltage image, a tube voltage at the time of imaging, the absorption coefficient of fat, and the absorption coefficient of mammary gland.

16 Claims, 8 Drawing Sheets

(51) Int. Cl.
    *G06T 7/00*           (2017.01)
    *A61B 5/107*         (2006.01)
    *A61B 6/04*          (2006.01)

(52) U.S. Cl.
    CPC .......... *A61B 5/4872* (2013.01); *A61B 6/5217* (2013.01); *G06T 7/0014* (2013.01); *A61B 5/1073* (2013.01); *A61B 6/0414* (2013.01); *G06T 2207/10116* (2013.01); *G06T 2207/20021* (2013.01); *G06T 2207/30068* (2013.01)

(58) Field of Classification Search
    USPC ....................................................... 378/5, 37
    See application file for complete search history.

(56) References Cited

U.S. PATENT DOCUMENTS

| | | | |
|---|---|---|---|
| 8,600,126 B2 | 12/2013 | Morita | |
| 8,738,124 B2 | 5/2014 | Davies | |
| 9,168,013 B2 | 10/2015 | Roessl et al. | |
| 2004/0247166 A1* | 12/2004 | Giger | G06F 19/321 382/128 |
| 2005/0004458 A1* | 1/2005 | Kanayama | A61B 5/0091 600/437 |
| 2006/0029268 A1* | 2/2006 | Endo | A61B 6/463 382/132 |
| 2008/0075228 A1* | 3/2008 | Tasaki | A61B 6/4494 378/37 |
| 2008/0080671 A1* | 4/2008 | Nakayama | A61B 6/502 378/97 |
| 2008/0240346 A1* | 10/2008 | Kashiwagi | A61B 6/502 378/37 |
| 2009/0086891 A1* | 4/2009 | Ofuji | A61B 6/463 378/37 |
| 2009/0118614 A1* | 5/2009 | Sendai | A61B 5/0077 600/437 |
| 2009/0214096 A1* | 8/2009 | Andrushkiw | G06T 7/0012 382/131 |
| 2009/0252396 A1* | 10/2009 | Morita | G06T 5/008 382/132 |
| 2010/0246924 A1* | 9/2010 | Morita | A61B 5/4872 382/132 |
| 2010/0321404 A1* | 12/2010 | Fischer | A61B 6/583 345/632 |
| 2011/0229006 A1* | 9/2011 | Morita | G06T 7/0012 382/132 |
| 2012/0189091 A1* | 7/2012 | Jerebko | A61B 6/025 378/4 |
| 2012/0238870 A1 | 9/2012 | Smith et al. | |
| 2013/0272595 A1* | 10/2013 | Heine | A61B 5/4312 382/132 |
| 2014/0254757 A1* | 9/2014 | Oh | A61B 6/484 378/62 |
| 2014/0270064 A1* | 9/2014 | Oh | A61B 6/482 378/53 |
| 2015/0093013 A1* | 4/2015 | Morita | A61B 6/502 382/132 |
| 2015/0327826 A1 | 11/2015 | Smith et al. | |
| 2015/0327829 A1* | 11/2015 | Morita | A61B 6/0414 378/37 |
| 2016/0174922 A1* | 6/2016 | Kodera | A61B 6/4035 378/37 |
| 2016/0213344 A1* | 7/2016 | Yi | A61B 6/5282 |
| 2016/0235379 A1 | 8/2016 | Homann | |
| 2016/0350910 A1* | 12/2016 | Jeong | G06K 9/52 |
| 2019/0290221 A1 | 9/2019 | Smith et al. | |

FOREIGN PATENT DOCUMENTS

| | | |
|---|---|---|
| JP | 2011505966 | 3/2011 |
| JP | 2013545575 | 12/2013 |
| JP | 2014507250 | 3/2014 |
| JP | 2016-535622 | 11/2016 |

\* cited by examiner

MAMMARY GLAND AMOUNT ACQUISITION APPARATUS, METHOD, AND PROGRAM

CROSS-REFERENCE TO RELATED APPLICATIONS

The present application claims priority under 35 U.S.C. § 119 to Japanese Patent Application No. 2017-065097, filed on Mar. 29, 2017. Each of the above application(s) is hereby expressly incorporated by reference, in its entirety, into the present application.

BACKGROUND OF THE INVENTION

1. Field of the Invention

The present invention relates to a mammary gland amount acquisition apparatus, method, and a non-transitory computer readable recording medium storing program for acquiring the amount of mammary gland contained in the breast based on two radiographic images acquired by radiations transmitted through the breast that have different energy distributions.

2. Description of the Related Art

In the related art, a radiographic image capturing apparatus (called a mammography apparatus) for imaging the breast is used. In mammography, the breast is placed on the imaging table, and imaging is performed in a state in which the breast is compressed by a compression plate. The breast is mainly formed of mammary gland tissues and adipose tissues, and it is important for diagnosis to find a lesion hidden in the mammary gland tissue. Therefore, by generating an energy subtraction image in which the mammary gland tissue in the breast has been extracted, it is possible to find a lesion hidden in the mammary gland tissue.

Energy subtraction processing in mammography is performed as follows. That is, by using the fact that mammary gland and fat forming the breast have different radiation absorbances for radiations having different energies, radiations having different energies are emitted to the breast to obtain two radiographic images. Then, an energy subtraction image in which adipose tissue has been removed and mammary gland tissue has been extracted is acquired by multiplying the two radiographic images by a weighting coefficient and then performing subtraction therebetween.

Here, the proportion of mammary gland in the breast is called a mammary gland content rate. The mammary gland content rate is very useful for accurately ascertaining the characteristics of the breast, and this is medically indispensable information. For example, research suggests that there is a correlation between the mammary gland content rate and the risk of carcinogenesis. For this reason, various methods for calculating the mammary gland content rate have been proposed. For example, JP2010-253245A has proposed a method in which a fat image, which is an image having a pixel value in a case where all mammary gland tissues of the breast are replaced with adipose tissues, is generated from a breast image acquired by mammography and the mammary gland content rate is calculated based on the relationship between the breast image and the fat image. In a case where the mammary gland content rate can be calculated, the mammary gland amount can also be calculated by multiplying the thickness of the breast by the mammary gland content rate.

The attenuation of the radiation transmitted through the breast changes depending on the amount of mammary gland contained in the breast. Therefore, a method of calculating the mammary gland amount based on the attenuation amount of radiation transmitted through the breast in the case of performing pre-shot imaging, in which imaging is performed with a low dose of radiation, in order to perform the positioning of the subject or the like has been proposed (refer to JP2016-535622A).

SUMMARY OF THE INVENTION

However, in the method of calculating the mammary gland amount from only one radiographic image as disclosed in JP2010-253245A and the method of calculating the mammary gland amount based on the attenuation of radiation as disclosed in JP2016-535622A, there is an influence of errors due to deflection and inclination of the compression plate used at the time of imaging. For this reason, in the methods disclosed in JP2010-253245A and JP2016-535622A, the calculation accuracy of the mammary gland amount is low.

The invention has been made in view of the above circumstances, and it is an object of the invention to accurately calculate the mammary gland amount of the breast.

A mammary gland amount acquisition apparatus according to the invention comprises: an image acquisition unit that acquires two radiographic images acquired by radiations transmitted through a breast that have different energy distributions; and a mammary gland amount calculation unit that calculates an amount of mammary gland contained in the breast based on the two radiographic images.

In the mammary gland amount acquisition apparatus according to the invention, the mammary gland amount calculation unit may comprise: a subject information acquisition unit that acquires a temporary thickness and a temporary mammary gland amount of the breast; an absorption coefficient acquisition unit that acquires a fat absorption coefficient corresponding to the temporary thickness and the temporary mammary gland amount of the breast and a mammary gland absorption coefficient corresponding to the temporary thickness and the temporary mammary gland amount of the breast with reference to a relationship between a thickness of the breast and a fat absorption coefficient and a relationship between the thickness of the breast and a mammary gland absorption coefficient, which are calculated in advance according to fat forming the breast and mammary gland forming the breast, and the energy distributions; and a calculation unit that calculates a new thickness and a new mammary gland amount of the breast based on the two radiographic images, a tube voltage at a time of imaging, the fat absorption coefficient, and the mammary gland absorption coefficient.

The "fat absorption coefficient" is a radiation absorption coefficient of fat, and the "mammary gland absorption coefficient" is a radiation absorption coefficient of mammary gland.

In the mammary gland amount acquisition apparatus according to the invention, the absorption coefficient acquisition unit may acquire a new fat absorption coefficient and a new mammary gland absorption coefficient based on the new thickness and the new mammary gland amount of the breast, and the absorption coefficient acquisition unit and the calculation unit may calculate the thickness and the mammary gland amount of the breast by repeating i) calculation of a newer thickness and a newer mammary gland amount of the breast based on the new fat absorption coefficient and the new mammary gland absorption coefficient and ii) acquisition of a newer fat absorption coefficient and a newer mammary gland absorption coefficient based on the newer thickness and the newer mammary gland amount of the breast.

In the mammary gland amount acquisition apparatus according to the invention, the mammary gland amount calculation unit may calculate the mammary gland amount by performing registration between the two radiographic images.

In the mammary gland amount acquisition apparatus according to the invention, the mammary gland amount calculation unit may further calculate a mammary gland content rate.

The mammary gland amount acquisition apparatus according to the invention may further comprise a classification unit that classifies a state of the breast based on the mammary gland content rate.

The mammary gland amount acquisition apparatus according to the invention may further comprise an image processing unit that performs image processing according to the mammary gland amount on at least one of the two radiographic images or another radiographic image obtained from the two radiographic images.

"Another radiographic image obtained from two radiographic images" means one radiographic image obtained by performing calculation on the two radiographic images. For example, an energy subtraction image obtained by performing weighting and subtraction processing on the two radiographic images and an addition image obtained by performing weighting and addition processing on the two radiographic images can be mentioned.

The mammary gland amount acquisition apparatus according to the invention may further comprise an index generation unit that generates an index indicating a possibility of disease occurrence according to the mammary gland amount.

In the mammary gland amount acquisition apparatus according to the invention, an exposure dose to the breast at a time of acquiring a radiographic image having a higher energy distribution between the two radiographic images may be smaller than an exposure dose to the breast at a time of acquiring a radiographic image having a lower energy distribution.

In the mammary gland amount acquisition apparatus according to the invention, a radiographic image having a higher energy distribution between the two radiographic images may be a pre-shot image.

At the time of capturing a radiographic image, in order to perform the positioning of the subject or the like, pre-shot imaging may be performed in which imaging is performed with a low dose of radiation. The "pre-shot image" is an image acquired by such pre-shot imaging. In a case where a radiographic image having a high energy distribution is assumed to be a pre-shot image, a radiographic image having a low energy distribution may be acquired by main imaging performed after pre-shot imaging.

In the mammary gland amount acquisition apparatus according to the invention, a radiographic image having the high energy distribution between the two radiographic images may be one of a plurality of projection images acquired by tomosynthesis imaging of the breast.

In the mammary gland amount acquisition apparatus according to the invention, a radiographic image having the high energy distribution between the two radiographic images may be a composite image that is generated by combining a plurality of tomographic images which are reconstructed from a plurality of projection images acquired by tomosynthesis imaging of the breast.

A mammary gland amount acquisition method according to the invention comprises: acquiring two radiographic images acquired by radiations transmitted through a breast that have different energy distributions; and calculating an amount of mammary gland contained in the breast based on the two radiographic images.

In addition, a non-transitory computer readable recording medium storing a program causing a computer to execute the mammary gland amount acquisition method according to the invention may be provided.

Another mammary gland amount acquisition apparatus according to the invention comprises: a memory that stores commands to be executed by a computer; and a processor that is configured to execute the stored commands and that performs processing for acquiring two radiographic images acquired by radiations transmitted through a breast that have different energy distributions and calculating an amount of mammary gland contained in the breast based on the two radiographic images.

According to the invention, two radiographic images acquired by radiations transmitted through the breast that have different energy distributions are acquired, and the amount of mammary gland contained in the breast is calculated based on the two radiographic images. Therefore, in the invention, since two images having different energy distributions are used, an error from the actual mammary gland amount can be reduced compared with a case where only one radiographic image is used. As a result, it is possible to accurately calculate the mammary gland amount.

DESCRIPTION OF THE PREFERRED EMBODIMENTS

Hereinafter, embodiments of the invention will be described with reference to the accompanying diagrams.

Figure 1:
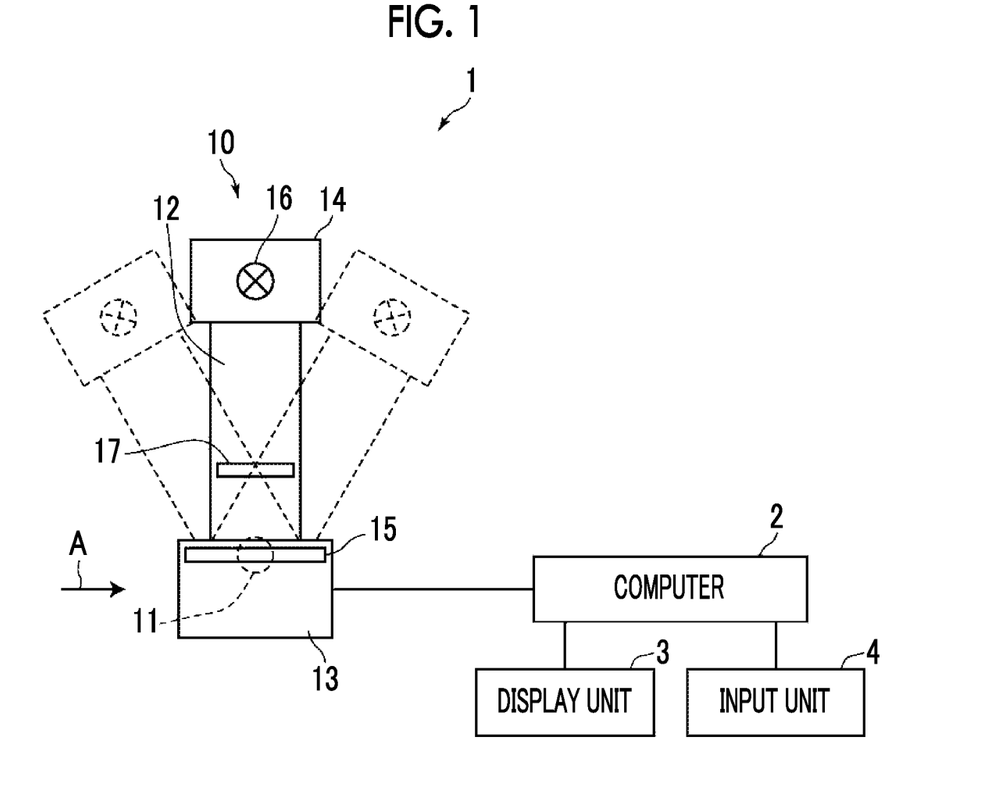
FIG. 1 is a diagram showing the schematic configuration of a radiographic image capturing apparatus to which a mammary gland amount acquisition apparatus according to a first embodiment of the invention is applied.
Figure 2:
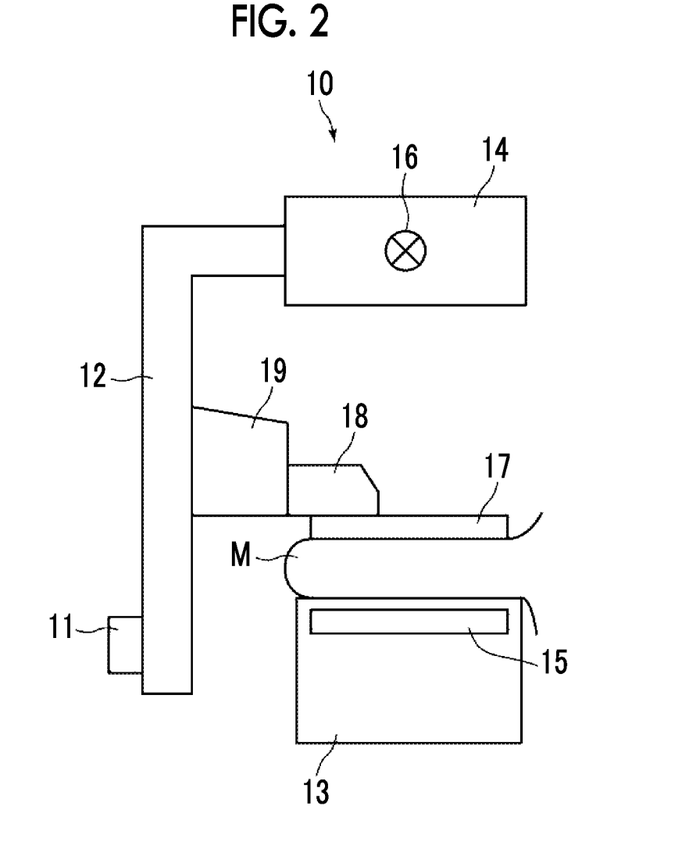
FIG. 2 is a diagram of the radiographic image capturing apparatus as viewed from the direction of arrow A in FIG. 1.

FIG. 1 is a schematic configuration diagram of a radiographic image capturing apparatus to which a mammary gland amount acquisition apparatus according to a first embodiment of the invention is applied, and FIG. 2 is a diagram of the radiographic image capturing apparatus as viewed from the direction of arrow A in FIG. 1. A radiographic image capturing apparatus 1 is a mammography apparatus for imaging a breast M that is a subject. In the present embodiment, similarly to a case of performing energy subtraction imaging of the breast M, radiations having different energy distributions are emitted to the breast M, which is a subject, to acquire a low voltage image based on low energy radiation and a high voltage image based on high energy radiation. As shown in FIG. 1, the radiographic image capturing apparatus 1 includes an imaging unit 10, a computer 2 connected to the imaging unit 10, and a display unit 3 and an input unit 4 connected to the computer 2.

The imaging unit 10 includes an arm unit 12 connected to a base (not shown) by a rotary shaft 11. An imaging table 13 is attached to one end portion of the arm unit 12, and an irradiation unit 14 is attached to the other end portion so as to face the imaging table 13. The arm unit 12 is configured to be able to rotate only the end portion to which the irradiation unit 14 is attached. Therefore, it is possible to rotate only the irradiation unit 14 with the imaging table 13 fixed. The rotation of the arm unit 12 is controlled by the computer 2.

By rotating the arm unit 12 in this manner, the radiographic image capturing apparatus 1 according to the present embodiment can acquire a tomographic image of the breast M by performing tomosynthesis imaging. The tomosynthesis imaging is a method in which, in order to observe an affected part in more detail, a radiation source is moved to irradiate a subject with radiation from a plurality of radiation source positions to perform imaging and a tomographic image emphasizing a desired tomographic plane is generated from a plurality of projection images acquired as described above. In tomosynthesis imaging, a plurality of projection images are acquired by imaging the subject at a plurality of radiation source positions by moving the radiation source in parallel with a radiation detector or so as to draw a circular or elliptical arc according to the characteristics of the imaging apparatus or required tomographic images and the projection images are reconstructed using a reconstruction method, such as a shift addition method, a simple back projection method, or a filtered back projection method (FBP method), to generate a tomographic image. In the present embodiment, explanation will be given on the assumption that the radiographic image capturing apparatus 1 acquires a low voltage image based on low energy radiation and a high voltage image based on high energy radiation instead of tomosynthesis imaging.

A radiation detector 15, such as a flat panel detector, is provided inside the imaging table 13. In addition, a circuit board on which a charge amplifier for converting a charge signal read from the radiation detector 15 into a voltage signal, a correlated double sampling circuit for sampling a voltage signal output from the charge amplifier, an AD conversion unit for converting a voltage signal into a digital signal, and the like are provided is provided inside the imaging table 13.

The radiation detector 15 can perform recording and reading of a radiographic image repeatedly. A so-called direct type radiation detector that generates an electric charge by direct reception of radiation may be used, or a so-called indirect type radiation detector that converts radiation into visible light and then converts the visible light into a charge signal may be used. As a method of reading a radiographic image signal, it is desirable to use a so-called TFT reading method in which a radiographic image signal is read by ON and OFF of a thin film transistor (TFT) switch or a so-called optical reading method in which a radiographic image signal is read by emission of reading light. However, other methods may also be used without being limited to the above methods.

An X-ray source 16, which is a radiation source, is housed inside the irradiation unit 14. The timing of emission of X-rays, which are radiations from the X-ray source 16, and X-ray generation conditions in the X-ray source 16, that is, imaging conditions such as a tube voltage and irradiation time, are controlled by the computer 2.

A compression plate 17 disposed above the imaging table 13 in order to compress the breast M, a support unit 18 for supporting the compression plate 17, and a moving mechanism 19 for moving the support unit 18 in the vertical direction in FIGS. 1 and 2 are provided at the arm unit 12. Information of the distance between the compression plate 17 and the imaging table 13, that is, information of the height of the compression plate 17, is input to the computer 2.

The display unit 3 is a display device, such as a cathode ray tube (CRT) or a liquid crystal monitor, and displays a subtraction image obtained as will be described later, a message required for the operation, and the like. The display unit 3 may include a speaker to output sound.

The input unit 4 is a keyboard, a mouse, or a touch panel type input device, and receives an operation on the radiographic image capturing apparatus 1 by the operator. In addition, the input unit 4 receives an input of various kinds of information, such as imaging conditions, and an instruction to modify the information, which are required to perform energy subtraction imaging. In the present embodiment, each unit of the radiographic image capturing apparatus 1 operates according to the information input from the input unit 4 by the operator.

A mammary gland amount acquisition program is installed on the computer 2. In the present embodiment, the computer may be a workstation or a personal computer that is directly operated by the operator, or may be a server computer connected to these through a network. The mammary gland amount acquisition program is distributed by being recorded on a recording medium, such as a digital versatile disc (DVD) and a compact disc read only memory (CD-ROM), and is installed on the computer from the recording medium. Alternatively, the mammary gland amount acquisition program is stored in a storage device of a server computer connected to the network or in a network storage so as to be accessible from the outside, and is downloaded and installed on the computer as necessary.

Figure 3:
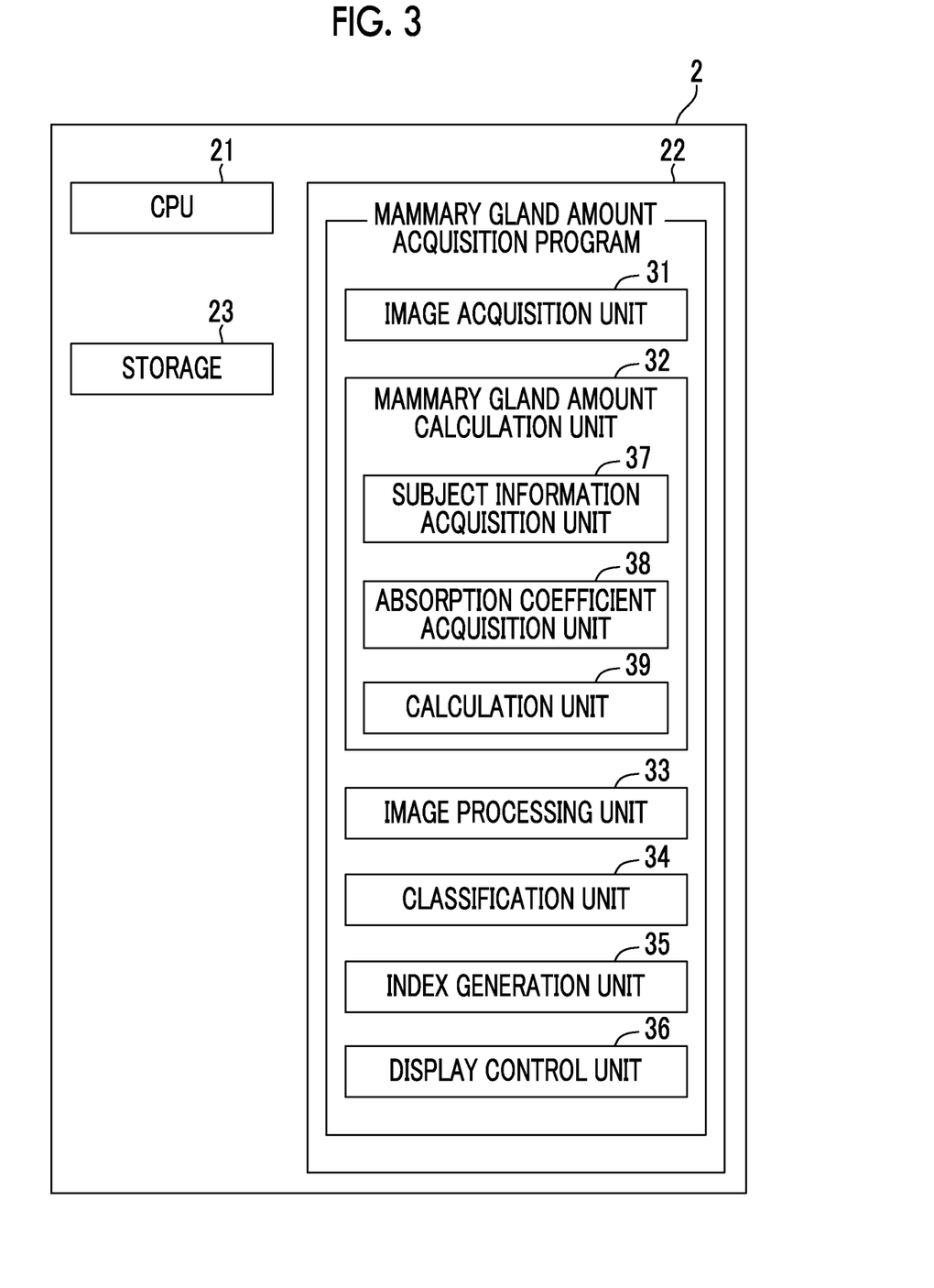
FIG. 3 is a diagram showing the schematic configuration of the mammary gland amount acquisition apparatus according to the first embodiment.

FIG. 3 is a diagram showing the schematic configuration of a mammary gland amount acquisition apparatus realized by installing the mammary gland amount acquisition program on the computer 2. As shown in FIG. 3, the mammary gland amount acquisition apparatus includes a central processing unit (CPU) 21, a memory 22, and a storage 23 as the configuration of a standard computer.

The storage 23 is a storage device, such as a hard disk or a solid state drive (SSD), and stores various kinds of information including a program for driving each unit of the radiographic image capturing apparatus 1 and a mammary gland amount acquisition program. A low voltage image and a high voltage image acquired by imaging are also stored. Various tables to be described later are also stored in the storage 23.

The memory 22 temporarily stores programs and the like stored in the storage 23 so that the CPU 21 execute various kinds of processing. As processing to be executed by the CPU 21, the mammary gland amount acquisition program defines: image acquisition processing for acquiring two radiographic images of a low voltage image GL and a high voltage image GH by causing the radiographic image capturing apparatus 1 to perform imaging; mammary gland amount calculation processing for calculating the amount of mammary gland contained in the breast M based on the low voltage image GL and the high voltage image GH; image processing performed on at least one of the low voltage image GL or the high voltage image GH according to the mammary gland amount; classification processing for classifying the state of the breast M based on the mammary gland content rate; index generation processing for generating an index indicating the possibility of disease occurrence according to the mammary gland amount; and display control processing for displaying an image subjected to the image processing, a classification result, an index, and the like on the display unit 3.

In addition, as processing to be executed by the CPU 21, the mammary gland amount acquisition program defines: subject information acquisition processing for acquiring the temporary thickness and the temporary mammary gland amount of the breast M; absorption coefficient acquisition processing for acquiring a fat absorption coefficient corresponding to the temporary thickness and the temporary mammary gland amount of the breast M and a mammary gland absorption coefficient corresponding to the temporary thickness and the temporary mammary gland amount of the breast M; and calculation processing for calculating the new thickness and the new mammary gland amount of the breast M based on the low voltage image, the high voltage image, the tube voltage at the time of imaging, the fat absorption coefficient, and the mammary gland absorption coefficient. The absorption coefficient acquisition processing is a process of acquiring the fat absorption coefficient corresponding to the temporary thickness and the temporary mammary gland amount of the breast M and the mammary gland absorption coefficient corresponding to the temporary thickness and the temporary mammary gland amount of the breast M with reference to the relationship between the thickness of the breast M and the fat absorption coefficient and the relationship between the thickness of the breast M and the mammary gland absorption coefficient, which are calculated in advance according to the fat forming the breast M and the mammary gland forming the breast M, and the energy distribution.

The CPU 21 executes these processes according to the mammary gland amount acquisition program, so that the computer 2 functions as an image acquisition unit 31, a mammary gland amount calculation unit 32, an image processing unit 33, a classification unit 34, an index generation unit 35, a display control unit 36, a subject information acquisition unit 37, an absorption coefficient acquisition unit 38, and a calculation unit 39. The computer 2 may include a processor or a processing circuit that performs image acquisition processing, mammary gland amount calculation processing, image processing, classification processing, index generation processing, display control processing, and subject information acquisition processing, absorption coefficient acquisition processing, and calculation processing in the mammary gland amount calculation processing.

The image acquisition unit 31 controls the irradiation unit 14 to emit two types of radiations having different energy distributions, thereby imaging the breast M in the same manner as in a so-called two-shot method in energy subtraction imaging. Specifically, low voltage imaging using X-rays of relatively low energy and high voltage imaging using X-rays of relatively high energy are performed. In the low voltage imaging, the X-ray source 16 is driven under the imaging conditions in which X-rays of relatively low energy are emitted (for example, a tube voltage of the X-ray source 16 is set to 26 kV) so that the X-rays are emitted to the breast M, and X-rays transmitted through the breast M are detected by the radiation detector 15, thereby acquiring the low voltage image GL. In the high voltage imaging, the X-ray source 16 is driven under the imaging conditions in which X-rays of relatively high energy are emitted (for example, a tube voltage of the X-ray source 16 is set to 45 kV) and the exposure dose to the breast M is lower than that in the low voltage imaging so that the X-rays are emitted to the breast M, and X-rays transmitted through the breast M are detected by the radiation detector 15, thereby acquiring the high voltage image GH. Alternatively, the low voltage image GL and the high voltage image GH may be acquired by using a one-shot method in which two radiation detectors 15 are disposed so as to overlap each other inside the imaging table 13 and X-rays transmitted through the breast M are simultaneously emitted to the two radiation detectors 15 overlapping each other so that X-rays having different energy distributions are emitted to the two radiation detectors 15.

Figure 4:
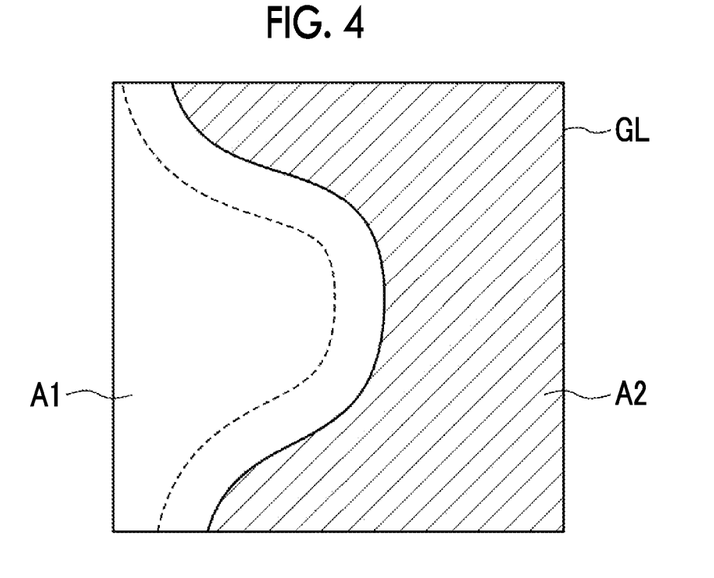
FIG. 4 is a diagram illustrating the detection of a breast region.

The subject information acquisition unit 37 of the mammary gland amount calculation unit 32 acquires the temporary thickness and the temporary mammary gland amount of the breast M. For the temporary thickness of the breast M, in the present embodiment, the temporary thickness of the breast M is acquired based on at least one of the low voltage image GL or the high voltage image GH. In the present embodiment, the temporary thickness of the breast M is acquired based on the low voltage image GL. The subject information acquisition unit 37 detects a region of the breast M from the low voltage image GL first. FIG. 4 is a diagram illustrating the detection of the region of the breast M. As shown in FIG. 4, the low voltage image GL includes a region A1 of the breast M and a blank region A2 which is a region where X-rays are directly emitted to the radiation detector 15. Here, the blank region A2 has a higher density than the region A1 of the breast. Therefore, by performing threshold processing on the low voltage image GL, it is possible to detect the region A1 of the breast M.

Figure 5:
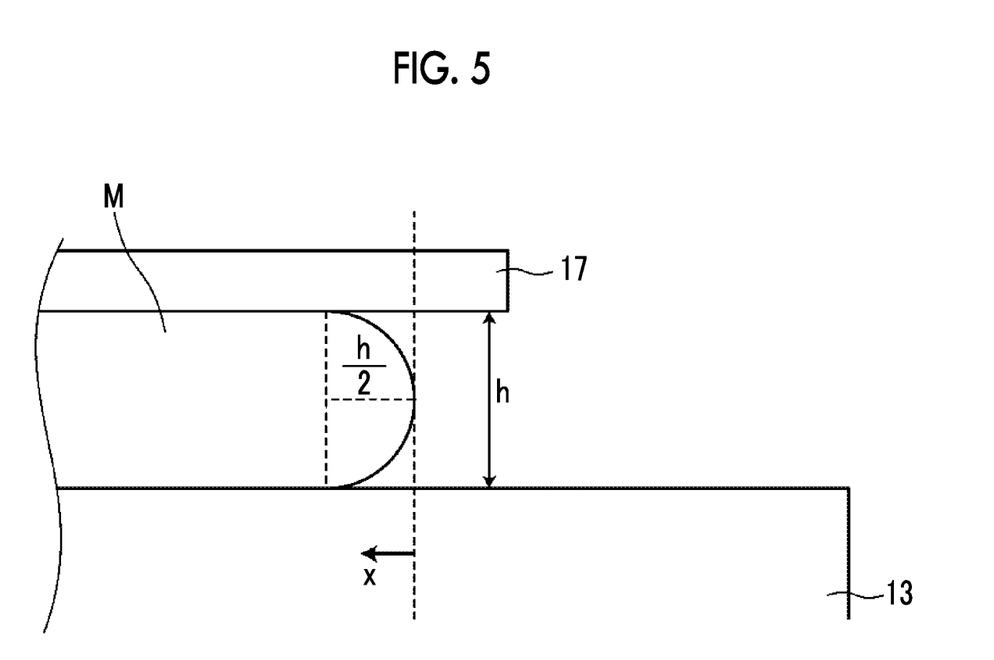
FIG. 5 is a diagram showing the breast interposed between a compression plate and an imaging table.

As shown in FIG. 5, the breast M is interposed between the imaging table 13 and the compression plate 17 at the time of imaging. Therefore, in the vicinity of a boundary between the region A1 of the breast and the blank region A2 (hereinafter, the boundary is referred to as a skin line) in the image acquired by imaging, the breast M is in contact with neither the imaging table 13 nor the compression plate 17. The subject information acquisition unit 37 acquires information of the height of the compression plate 17 from the imaging unit 10. Here, it is assumed that the cross-sectional shape of the breast M in the vicinity of the skin line of the breast M is semicircular. Assuming that the height of the compression plate 17 is h, in a region exceeding h/2 from the skin line in the region A1 of the breast M acquired from the low voltage image GL, the height h of the compression plate 17 is acquired as the thickness of the breast M. A position at the distance h/2 from the skin line is shown by a broken line. On the other hand, in a region from the skin line to the distance h/2, the temporary thickness of the breast M is acquired by calculating a thickness R according to the following Equation (1) with the distance from the skin line being x.

$$R = (0.5h - x)\sqrt{\left(\frac{0.5h}{0.5h - x}\right)^2 - 1} \quad (1)$$

Next, acquisition of the temporary mammary gland amount will be described. In the present embodiment, the subject information acquisition unit 37 calculates the mammary gland content rate from the low voltage image GL using the method disclosed in JP2010-253245A, for example. In the method disclosed in JP2010-253245A, the temporary mammary gland content rate is calculated from the low voltage image GL as follows. First, in the low voltage image GL, a fat image that is an image having a pixel value in a case where all mammary gland tissues of the breast M are replaced with adipose tissues is generated. Then, based on the low voltage image GL, the fat image, the pixel value of the blank region A2 in the low voltage image GL, and a ratio between the average attenuation coefficient of the mammary gland and the average attenuation coefficient of fat stored in the storage 23, the mammary gland content rate is calculated for each pixel of the low voltage image GL. Then, the subject information acquisition unit 37 calculates the temporary mammary gland amount by multiplying the thickness of the breast M by the mammary gland content rate. The mammary gland content rate is not limited to that calculated as described above. For example, the mammary gland content rate may be set to a predetermined value (for example, 50%).

Figure 6:
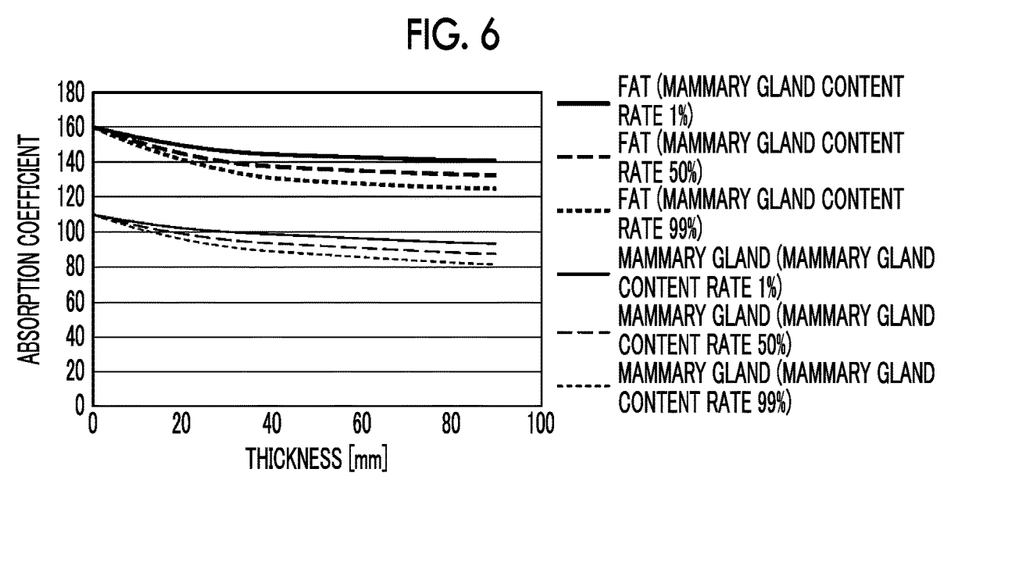
FIG. 6 is a diagram showing the relationship between the breast thickness and an X-ray absorption coefficient calculated in advance according to the substance forming the breast (low energy).
Figure 7:
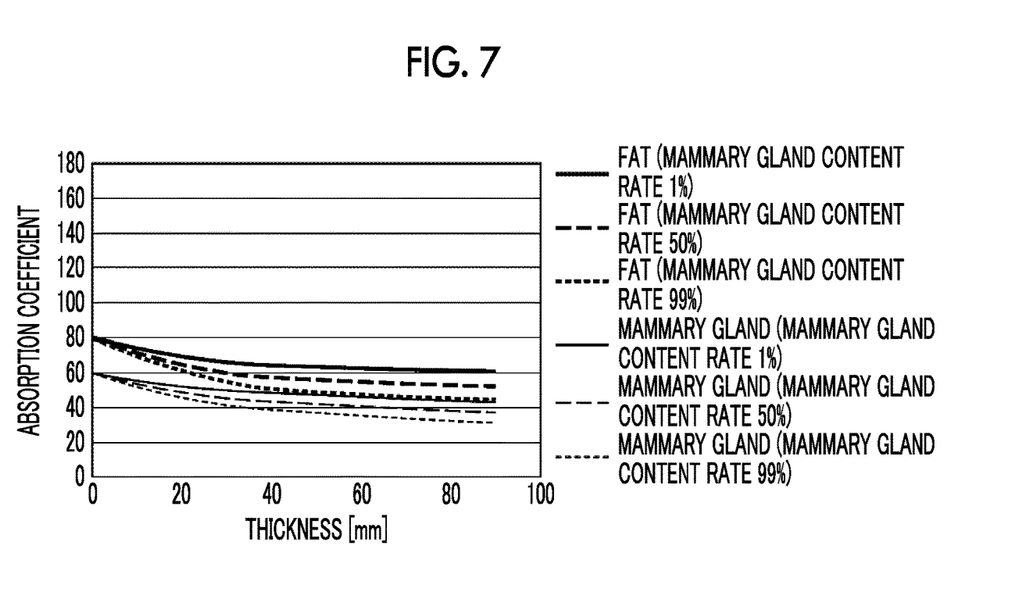
FIG. 7 is a diagram showing the relationship between the breast thickness and an X-ray absorption coefficient calculated in advance according to the substance forming the breast (high energy).

The absorption coefficient acquisition unit 38 acquires an absorption coefficient corresponding to the subject information with reference to the relationship between the thickness of the breast M and the X-ray absorption coefficient, which is calculated in advance according to the energy distribution and the substance forming the breast M. In the present embodiment, the relationship between the thickness of the breast M and the X-ray absorption coefficient, which is calculated in advance according to the energy distribution and the substance forming the breast M, is stored in the storage 23. FIGS. 6 and 7 are diagrams showing the relationship between the thickness of the breast M and the X-ray absorption coefficient, which is calculated in advance according to the substance forming the breast M. FIG. 6 shows an absorption coefficient with respect to low energy X-rays as the energy distribution, and FIG. 7 shows an absorption coefficient with respect to high energy X-rays as the energy distribution. As shown in FIGS. 6 and 7, the relationship between the thickness of the breast M and the absorption coefficient is stored in the storage 23 for each of fat and mammary gland forming the breast M. Here, the absorption coefficient of the substance is determined depending on the energy of X-rays. In a process in which X-rays are transmitted through the subject, the low energy component of the X-rays is absorbed by the subject. As a result, beam hardening that causes increasing ratio of high energy X-rays occurs. Therefore, as shown in FIGS. 6 and 7, the absorption coefficient decreases as the thickness of the breast M increases. The beam hardening differs depending on the composition of the subject. In a case where the subject is the breast M, as shown in FIGS. 6 and 7, the absorption coefficient decreases as the mammary gland content rate increases. In addition, the absorption coefficient decreases as the energy of X-rays increases.

Based on the relationship shown in FIGS. 6 and 7 and the mammary gland content rate used to calculate the temporary thickness and the temporary mammary gland amount of the breast M acquired by the subject information acquisition unit 37, the absorption coefficient acquisition unit 38 acquires the absorption coefficients of fat and mammary gland corresponding to the energy of X-rays and the temporary thickness of the breast M and the mammary gland content rate. Specifically, a mammary gland absorption coefficient $\mu_g^L$ and a fat absorption coefficient $\mu_a^L$ for low energy X-rays and a mammary gland absorption coefficient $\mu_g^H$ and a fat absorption coefficient $\mu_a^H$ for high energy X-rays are acquired.

FIGS. 6 and 7 show the relationship between the thickness of the breast M and the absorption coefficient in a case where the mammary gland content rate is 1%, 50%, and 99%. However, in a case where the mammary gland content rate is an intermediate value between these values, the absorption coefficient may be calculated by interpolation calculation.

The calculation unit 39 calculates the new thickness and the new mammary gland amount of the breast M based on the low voltage image GL, the high voltage image GH, the tube voltage at the time of imaging, the fat absorption coefficient, and the mammary gland absorption coefficient.

Figure 8:
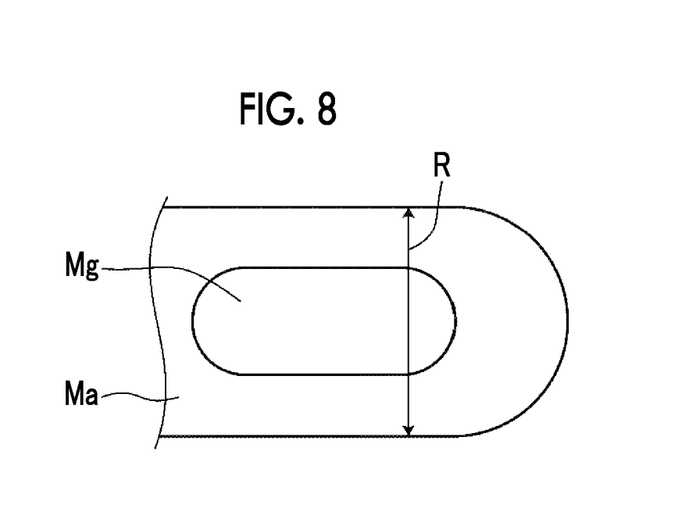
FIG. 8 is a diagram showing a cross section of a compressed breast.

FIG. 8 is a conceptual diagram illustrating the processing performed by the calculation unit. FIG. 8 is a conceptual diagram showing a cross section of the breast M in a state in which the breast M is compressed by the compression plate 17. In addition, FIG. 8 schematically shows a state in which fat Ma and mammary gland Mg are contained in the breast M. R in FIG. 8 indicates the thickness of the breast M. In order to accurately perform the processing shown below, the calculation unit 39 performs registration between the low voltage image GL and the high voltage image GH so that the corresponding pixel positions of the low voltage image GL and the high voltage image GH match each other. As shown in FIG. 8, in the breast M containing the fat Ma and the mammary gland Mg, the dose reaching the radiation detector 15 is expressed by the following Equation (2).

$$N \approx \phi_0(E_0)e^{-\mu_g(E_0)r_g - \mu_a(E_0)r_a} \quad (2)$$

Here, N is a dose at the time of acquiring a radiographic image, $\phi_0$ is a function indicating the dose and the sensitivity of a radiation detector, $E_0$ is a tube voltage of the X-ray source 16, $r_a$ is a fat thickness, $r_g$ is a mammary gland thickness, $\mu_a$ is an X-ray absorption coefficient of fat, and $\mu_g$ is an X-ray absorption coefficient of mammary gland.

Assuming that the tube voltages of the X-ray source 16 at the time of acquiring the low voltage image GL and the high voltage image GH are $E_L$ and $E_H$ and the doses reaching the radiation detector 15 at the time of acquiring the low voltage image GL and the high voltage image GH are $N^L$ and $N^H$, the doses $N^L$ and $N^H$ are calculated according to Equation (2) for the low voltage image GL and the high voltage image GH, respectively. By log converting the result, the following Equations (3) and (4) are obtained. $C_1$ and $C_2$ are constants.

$$\mathrm{LOG}(N^H) = -\mu_g^H(E_H)r_g - \mu_a^H(E_H)r_a + C_1 \quad (3)$$

$$\mathrm{LOG}(N^L) = -\mu_g^L(E_L)r_g - \mu_a^L(E_L)r_a + C_2 \quad (4)$$

Here, $N^L$ is a dose at the time of acquiring the low voltage image GL, $N^H$ is a dose at the time of acquiring the high voltage image GH, $E_L$ is a tube voltage of the X-ray source 16 at the time of low voltage imaging, $E_H$ is a tube voltage of the X-ray source 16 at the time of high voltage imaging, $\mu_a^L$ is a fat absorption coefficient for low energy X-rays, $\mu_g^L$ is a mammary gland absorption coefficient for low energy X-rays, $\mu_a^H$ is a fat absorption coefficient for high energy X-rays, and $\mu_g^H$ is a mammary gland absorption coefficient for high energy X-rays.

In this case, since the thickness R of the breast M is $R = r_a + r_g$, the thickness R is calculated according to the following Equation (5). $C_1$, $C_2$, and $C_3$ are constants determined according to the imaging conditions and the sensitivity of the radiation detector 15.

$$R = \beta * (\alpha * \mathrm{LOG}(N^H) - \mathrm{LOG}(N^L)) + C_3 \qquad (5)$$

Here, $$\beta = \left( \frac{\mu_g^H(E_H) - \mu_a^H(E_H)}{(\mu_g^L(E_L) - \mu_a^L(E_L))\mu_a^L(E_L) - (\mu_g^H(E_H) - \mu_a^E(E_H))\mu_g^H(E_H)} \right),$$

$$\alpha = \frac{\mu_g^L(E_L) - \mu_a^L(E_L)}{\mu_g^H(E_H) - \mu_a^H(E_H)}$$

In the present embodiment, the mammary gland absorption coefficient $\mu_g^L$ and the fat absorption coefficient $\mu_a^L$ for low energy X-rays and the mammary gland absorption coefficient $\mu_g^H$ and the fat absorption coefficient $\mu_a^H$ for high energy X-rays are acquired by the absorption coefficient acquisition unit 38. Based on the signal values at the respective pixel positions of the low voltage image GL and the high voltage image GH, the calculation unit 39 acquires the dose $N^L$ at the time of acquiring the low voltage image GL and the dose $N^H$ at the time of acquiring the high voltage image GH. The dose is acquired for each pixel position. Then, the calculation unit 39 substitutes the acquired absorption coefficients and doses into Equations (3) and (4). Then, by solving Equations (3) and (4) for $r_a$ and $r_g$, the thickness $r_a$ of fat and the thickness $r_g$ of mammary gland are calculated for each pixel position. Then, by substituting the calculated thickness $r_a$ of fat and the calculated thickness $r_g$ of mammary gland into Equation (5), the thickness R of the breast M at each pixel position is calculated. The calculated thickness R becomes the new thickness of the breast M.

Here, since the thickness R of the breast M is $R = r_a + r_g$, $r_g = R - r_a$. Therefore, using the calculated thickness R of the breast M, the thickness $r_g$ of the mammary gland can be calculated according to Equation (4) to the following Equation (6). The thickness $r_g$ of the mammary gland becomes the new mammary gland amount. For this reason, $r_g$ may be used as a reference numeral of the mammary gland amount. Accordingly, the mammary gland content rate can be calculated by $r_g / R$.

$$r_g = \frac{1}{\mu_g^L(E_L) - \mu_a^L(E_L)} (C_2 - \mathrm{LOG}(N^L) - \mu_a^L(E_L) * R) \qquad (6)$$

As described above, the calculation unit 39 calculates the new thickness R, the new mammary gland amount, and the mammary gland content rate of the breast M. The calculation unit 39 calculates the volume of the breast M from the thickness R and the area of the breast M. The area of the breast M is a range up to the large pectoral muscle of the breast M included in the low voltage image GL or the high voltage image GH. The calculation unit 39 calculates the volume of the mammary gland from the mammary gland amount and the area of the breast M. The calculation unit 39 calculates the mammary gland content rate of the entire breast M by dividing the volume of the mammary gland by the volume of the breast M. By calculating the average value of the mammary gland content rate of each pixel, the mammary gland content rate of the entire breast M may be calculated.

The image processing unit 33 performs image processing on the low voltage image GL or the high voltage image GH based on the mammary gland content rate of the entire breast M calculated by the mammary gland amount calculation unit 32. In the present embodiment, contrast enhancement processing according to the mammary gland content rate is performed on the low voltage image GL. Here, as the mammary gland content rate increases, a lesion structure is hidden in the mammary gland in the radiographic image. For this reason, contrast enhancement processing is performed on the low voltage image GL so that the contrast increases as the mammary gland content rate increases. In addition to the contrast enhancement processing, the image processing unit 33 may perform density correction processing, frequency processing, and the like on the low voltage image GL.

The classification unit 34 classifies the state of the breast M based on the mammary gland content rate of the entire breast M calculated by the mammary gland amount calculation unit 32. Specifically, the state of the breast M is classified into "fatty" in a case where the mammary gland content rate is 0% or more and less than 15%, "mammary gland scattered" in a case where the mammary gland content rate is 15% or more and less than 35%, "uneven high density" in a case where the mammary gland content rate is 35% or more and less than 60%, and "high density" in a case where the mammary gland content rate is 60% or more.

The index generation unit 35 generates an index indicating the possibility of disease occurrence according to the mammary gland amount. In the present embodiment, the degree of risk of carcinogenesis according to the mammary gland content rate of the entire breast M calculated by the mammary gland amount calculation unit 32 is generated as an index. Specifically, the index generation unit 35 generates an index of "no risk" in a case where the mammary gland content rate is 0% or more and less than 15%, an index of "low risk" in a case where the mammary gland content rate is 15% or more and less than 35%, "medium risk" in a case where the mammary gland content rate is 35% or more and less than 60%, and "high risk" in a case where the mammary gland content rate is 60% or more.

Figure 9:
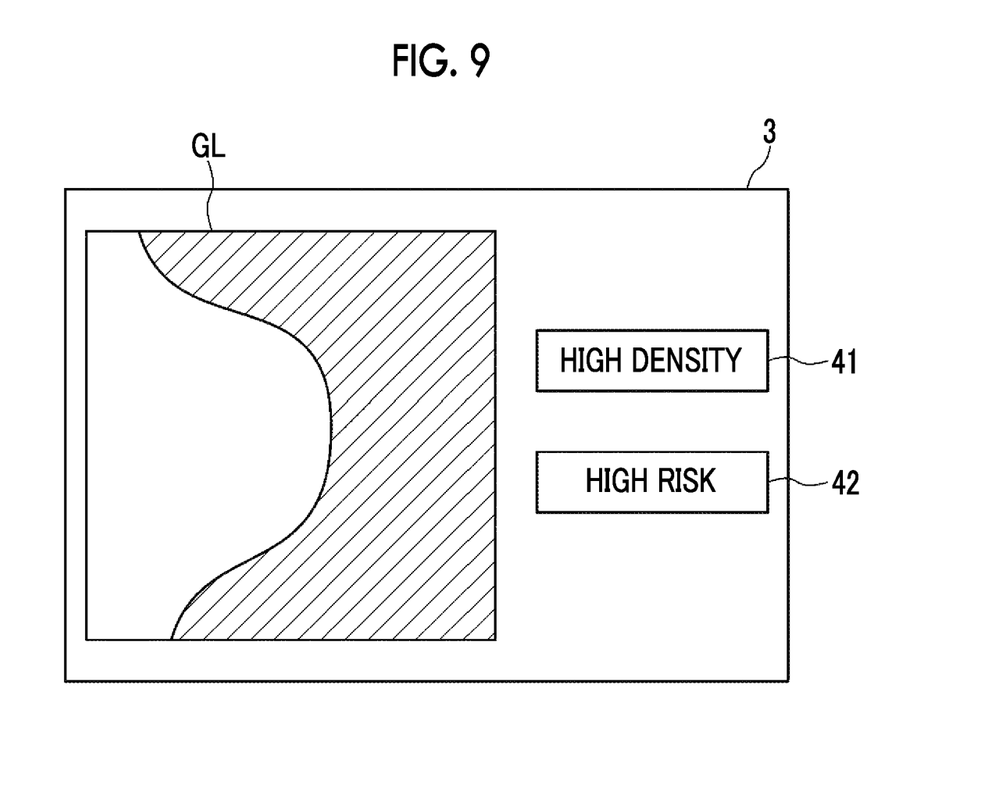
FIG. 9 is a diagram showing an examination result displayed on a display unit.

The display control unit 36 displays the low voltage image GL subjected to the image processing, the classification result of the classification unit 34, and the index generated by the index generation unit 35 on the display unit 3 as the examination result. FIG. 9 is a diagram showing the examination result displayed on the display unit 3. As shown in FIG. 9, the low voltage image GL subjected to the image processing, a classification result 41, and an index 42 are included in the display unit 3. In FIG. 9, the classification result is "high density", and the index is "high risk".

Figure 10:
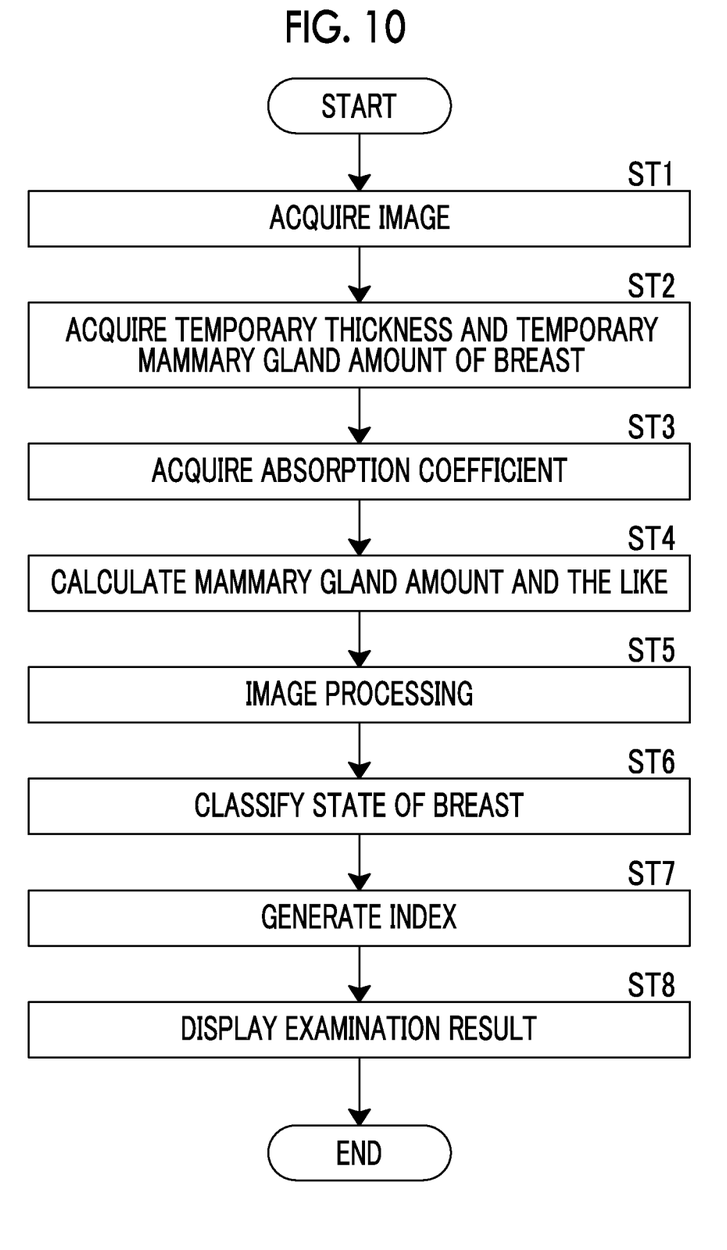
FIG. 10 is a flowchart showing the process performed in the first embodiment.

Next, the process performed in the first embodiment will be described. FIG. 10 is a flowchart showing the process performed in the first embodiment. In a case where the input unit 4 receives an operator's instruction to start the process, the breast M is imaged so that the image acquisition unit 31 acquires the low voltage image GL and the high voltage image GH (image acquisition: step ST1). Then, the subject information acquisition unit 37 of the mammary gland amount calculation unit 32 acquires the temporary thickness and the temporary mammary gland amount of the breast M based on the low voltage image GL (step ST2). Then, the absorption coefficient acquisition unit 38 acquires a fat absorption coefficient and a mammary gland absorption coefficient with reference to the relationship between the thickness of the breast M and the X-ray absorption coefficient, which is calculated in advance according to the energy distribution and the substance forming the breast M (absorption coefficient acquisition: step ST3). Then, based on the low voltage image GL, the high voltage image GH, the tube voltage at the time of imaging, the fat absorption coefficient, and the mammary gland absorption coefficient, the calculation unit 39 calculates the new thickness R and the new mammary gland amount of the breast M, and calculates the mammary gland content rate (mammary gland amount calculation; step ST4). Then, the image processing unit 33 performs image processing on the low voltage image GL according to the mammary gland amount (step ST5), and the classification unit 34 classifies the state of the breast M based on the mammary gland content rate of the entire breast M calculated by the mammary gland amount calculation unit 32 (step ST6). Then, the index generation unit 35 generates an index indicating the possibility of disease occurrence according to the mammary gland amount (step ST7). Then, the display control unit 36 displays the low voltage image GL subjected to the image processing, the classification result of the classification unit 34, and the index generated by the index generation unit 35 on the display unit 3 as the examination result (step ST8), and the process is ended.

As described above, in the first embodiment, since the amount of mammary gland contained in the breast is calculated based on the low voltage image GL and the high voltage image GH, an error from the actual value of the mammary gland amount can be reduced compared with a case where only one radiographic image is used. As a result, it is possible to accurately calculate the mammary gland amount.

In addition, since the registration between the low voltage image GL and the high voltage image GH is performed by the calculation unit 39, it is possible to calculate the mammary gland amount more accurately.

Here, as the mammary gland amount increases, a lesion is hidden in the mammary gland in the radiographic image. For this reason, by performing image processing according to the mammary gland amount, it is possible to increase the contrast or the like as the mammary gland amount increases. Therefore, a lesion can be easily found in the radiographic image regardless of the mammary gland amount.

The low voltage image GL has a higher contrast than the high voltage image GH. Therefore, based on the low voltage image GL, it is possible to accurately acquire the thickness and the mammary gland amount of the breast M.

Figure 11:
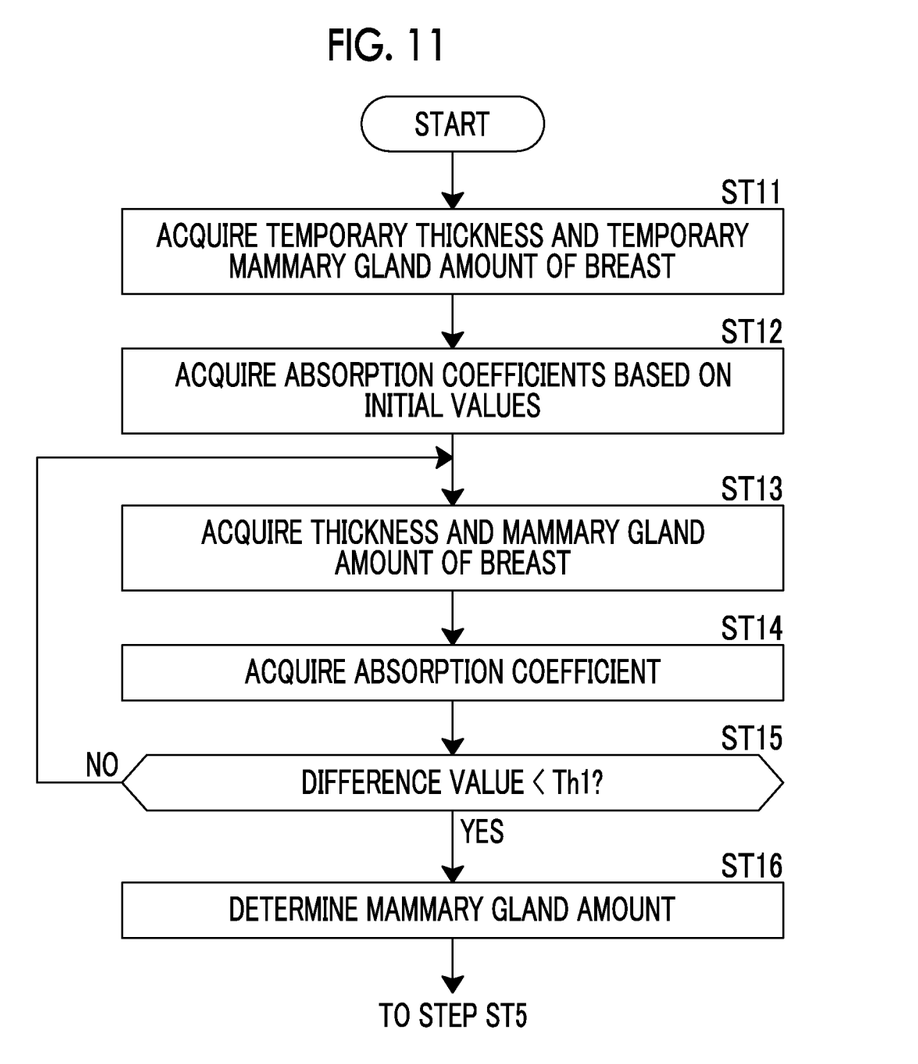
FIG. 11 is a flowchart showing the process performed in a second embodiment.

In the first embodiment described above, in order to acquire the more accurate thickness R and mammary gland amount of the breast M, which are suitable for the subject, repetitive calculation may be performed. Hereinafter, this will be described as a second embodiment. FIG. 11 is a flowchart of repetitive calculation in the second embodiment.

In the second embodiment, as in the first embodiment described above, the subject information acquisition unit 37 acquires the temporary thickness and the temporary mammary gland amount of the breast M (step ST11), and the absorption coefficient acquisition unit 38 acquires a fat absorption coefficient and a mammary gland absorption coefficient with these as initial values (absorption coefficient acquisition using initial values: step ST12). Then, the calculation unit 39 calculates the thickness R and the mammary gland amount $r_g$ of the breast M as in the first embodiment (step ST13). In the second embodiment, using the thickness R and the mammary gland amount $r_g$ calculated by the calculation unit 39, the fat absorption coefficient and the mammary gland absorption coefficient are acquired with reference to the relationship shown in FIGS. 6 and 7 (absorption coefficient acquisition: step ST14). Then, the calculation unit 39 determines whether or not a difference value between each of the fat absorption coefficient and the mammary gland absorption coefficient acquired in step ST14 and each of the fat absorption coefficient and the mammary gland absorption coefficient acquired in the previous processing is less than a threshold value Th1 (step ST15). In the first processing, the difference value is a difference between each of the fat absorption coefficient and the mammary gland absorption coefficient acquired in step ST14 and each of the fat absorption coefficient and the mammary gland absorption coefficient acquired using the thickness and the mammary gland amount of the breast M acquired by the subject information acquisition unit 37.

Here, the fat absorption coefficient $\mu_a^L$ for low energy X-rays, the mammary gland absorption coefficient $\mu_g^L$ for low energy X-rays, the fat absorption coefficient $\mu_a^H$ for high energy X-rays, and the mammary gland absorption coefficient $\mu_g^H$ for high energy X-rays are acquired as fat absorption coefficients and mammary gland absorption coefficients. Therefore, in the processing of step ST15, it is determined whether or not difference values for all the four absorption coefficients are less than the threshold value Th1. The threshold value Th1 may be set for each absorption coefficient. Here, it is assumed that step ST15 is affirmed in a case where all the four difference values are less than the threshold value Th1.

In a case where step ST15 is denied, the calculation unit 39 returns to step ST13 to calculate the new thickness R and the new mammary gland amount $r_g$ of the breast M and acquire a new fat absorption coefficient and a new mammary gland absorption coefficient using the thickness R and the mammary gland amount $r_g$ of the breast M calculated in step ST13 and the fat absorption coefficient and the mammary gland absorption coefficient acquired in step ST14. Then, the processing of steps ST13 and ST14 is repeated until step ST15 is affirmed. In a case where step ST15 is affirmed, the mammary gland amount $r_g$ calculated at that point in time is determined as a final mammary gland amount (step ST16). After step ST16, the processing from step ST5 in the first embodiment is performed.

As described above, in the second embodiment, since the thickness R and the mammary gland amount $r_g$ of the breast M are calculated by repetitive calculation and the fat absorption coefficient and the mammary gland absorption coefficient are acquired, it is possible to reduce errors between the calculated values and the actual values. As a result, it is possible to calculate the mammary gland amount more accurately.

In the second embodiment described above, every time the processing of steps ST13 and ST14 is repeated, it is determined whether or not the difference value between the absorption coefficients is less than the threshold value Th1 in step ST15. However, the processing of step ST15 may be performed every time the processing of steps ST13 and ST14 is repeated a predetermined first number of times. Alternatively, the processing of steps ST13 and ST14 may be repeated without performing the processing of step ST15 until a predetermined second number of times from the start of the process, and the processing of step ST15 may be performed every time the processing of steps ST13 and ST14 may be repeated after repeating the second number of times. Also in this case, after repeating the processing of steps ST13 and ST14 a second number of times, the processing of step ST15 may be performed every time the processing of steps ST13 and ST14 is repeated a predetermined first number of times.

In each of the embodiments described above, the low voltage image GL and the high voltage image GH are acquired. However, in order to perform the positioning of the subject or the like, pre-shot imaging may be performed in which imaging is performed with a low dose of radiation. In this case, the pre-shot imaging may be performed by using X-rays having energy higher than in the subsequent imaging (assumed to be main imaging), and a pre-shot image acquired by the pre-shot imaging may be used as the high voltage image GH. In this case, the radiographic image acquired by the main imaging may be used as the low voltage image GL.

In each of the embodiments described above, in the case of performing tomosynthesis imaging of the breast M, X-rays having energy higher than in the case of acquiring the low voltage image GL may be used, and one projection image acquired by tomosynthesis imaging may be used as the high voltage image GH. In this case, it is preferable to use a projection image acquired at a radiation source position, which is closest to that in the case of acquiring the low voltage image GL, as the high voltage image GH. A composite image that is generated by generating a plurality of tomographic images by reconstructing the projection image acquired by the tomosynthesis imaging, adding the plurality of tomographic images at corresponding pixel positions, and performing enlargement and reduction so as to have the same size as the low voltage image GL may be used as the high voltage image GH. In this case, it is preferable to generate a composite image by geometrically converting the plurality of tomographic images so that the high voltage image GH is acquired at the same radiation source position as in the case of acquiring the low voltage image GL.

At the time of imaging the breast M, as shown in FIG. 5, the vicinity of the skin line is not in close contact with the imaging table 13. For this reason, in a region between the broken line and the skin line in FIG. 4, the thickness R of the breast M is reduced. Therefore, in the low voltage image GL displayed on the display unit 3, the density increases in the vicinity of the skin line of the breast M. For this reason, the density of the low voltage image GL may be corrected by the image processing unit 33 using the thickness R of the breast M calculated according to the above Equation (5). In this case, the image processing unit 33 compares the thickness R of the breast M calculated by the calculation unit 39 for each pixel of the low voltage image GL. In the second embodiment, the thickness R of the breast M is the final thickness R. Then, in a pixel having a smaller thickness than other pixels, correction is made so that the density of the pixel value is close to the densities of the other pixels. Therefore, in the corrected low voltage image GL, the density in the vicinity of the skin line can be made to be the same as the densities in the other regions. As a result, it is possible to generate the low voltage image GL with higher image quality.

In each of the embodiments described above, an energy subtraction image may be generated by performing energy subtraction processing on the low voltage image GL and the high voltage image GH using the calculated absorption coefficients. In this case, the weighting coefficients for the low voltage image GL and the high voltage image GH are calculated based on the absorption coefficients acquired by the absorption coefficient acquisition unit 38 or the absorption coefficients calculated by the calculation unit 39. In the case of calculating a subtraction image Gs by subtracting the low voltage image GL from the high voltage image GH weighted by the weighting coefficient α according to the following Equation (7), the weighting coefficient α is calculated by the following Equation (8).

$$Gs = \alpha \cdot GH - GL \tag{7}$$

$$\alpha = (\mu_g^H - \mu_a^H)/(\mu_g^L - \mu_a^L) \tag{8}$$

The image processing unit 33 may perform image processing according to the mammary gland amount on the subtraction image Gs generated as described above, in the same manner as in the case of performing image processing on the low voltage image GL.

Hereinafter, the effect of the present embodiment will be described.

By acquiring a new fat absorption coefficient and a new mammary gland absorption coefficient based on the calculated thickness and mammary gland amount of the breast and calculating the thickness and the mammary gland amount of the breast by repeating the calculation of a new thickness and a new mammary gland amount of the breast based on the new fat absorption coefficient and the new mammary gland absorption coefficient and the acquisition of a newer fat absorption coefficient and a newer mammary gland absorption coefficient based on the new thickness and the new mammary gland amount of the breast, it is possible to reduce the error between the value of the calculated mammary gland amount and the value of the actual mammary gland amount. As a result, it is possible to calculate the mammary gland amount more accurately.

By calculating the mammary gland amount by performing registration between the two radiographic images, it is possible to calculate the mammary gland amount more accurately.

Here, as the mammary gland amount increases, a lesion is hidden in the mammary gland in the radiographic image. For this reason, by performing image processing according to the mammary gland amount, it is possible to increase the contrast or the like as the mammary gland amount increases. Therefore, a lesion can be easily found in the radiographic image regardless of the mammary gland amount.

EXPLANATION OF REFERENCES

1: radiographic image capturing apparatus
2: computer
3: display unit
4: input unit
10: imaging unit
11: rotary shaft
12: arm unit
13: imaging table
14: irradiation unit
15: radiation detector
16: X-ray source
17: compression plate
18: support unit
19: moving mechanism
21: CPU
22: memory
23: storage
31: image acquisition unit 32: mammary gland amount calculation unit
33: image processing unit
34: classification unit
35: index generation unit
36: display control unit
37: subject information acquisition unit
38: absorption coefficient acquisition unit
39: calculation unit
A1: breast region
A2: blank region
M: breast
Ma: fat
Mg: mammary gland
R: height of compression plate
GL: low voltage image
GH: high voltage image

What is claimed is:

1. A mammary gland amount acquisition apparatus, comprising:
a memory, configured to store a first relationship between thickness of breast and fat absorption coefficient and a second relationship between thickness of breast and mammary gland absorption coefficient; and
a processor, configured to:
acquire two radiographic images acquired by radiations transmitted through a breast, wherein the two radiographic images have different energy distributions;
acquire a first thickness of the breast using one of the radiographic images;
acquire a fat absorption coefficient using the first thickness and the first relationship;
acquire a mammary gland absorption coefficient using the first thickness and the second relationship; and
acquire an amount of mammary gland contained in the breast based on using the two radiographic images, the fat absorption coefficient, the first mammary gland absorption coefficient, and a tube voltage at a time of imaging the two radiographic images.

2. The mammary gland amount acquisition apparatus according to claim 1,
wherein the processor acquires a new fat absorption coefficient and a new mammary gland absorption coefficient based on a thickness and the mammary gland amount of the breast, and
the processor calculates the thickness and the mammary gland amount of the breast by repeating i) calculation of a newer thickness and a newer mammary gland amount of the breast based on the new fat absorption coefficient and the new mammary gland absorption coefficient and ii) acquisition of a newer fat absorption coefficient and a newer mammary gland absorption coefficient based on the newer thickness and the newer mammary gland amount of the breast.

3. The mammary gland amount acquisition apparatus according to claim 2,
wherein the processor calculates the mammary gland amount by performing registration between the two radiographic images.

4. The mammary gland amount acquisition apparatus according to claim 2,
wherein the processor further calculates a mammary gland content rate.

5. The mammary gland amount acquisition apparatus according to claim 1,
wherein the processor calculates the mammary gland amount by performing registration between the two radiographic images.

6. The mammary gland amount acquisition apparatus according to claim 5,
wherein the processor further calculates a mammary gland content rate.

7. The mammary gland amount acquisition apparatus according to claim 1,
wherein the processor further calculates a mammary gland content rate.

8. The mammary gland amount acquisition apparatus according to claim 7, wherein the processor is further configured to:
classify a state of the breast based on the mammary gland content rate.

9. The mammary gland amount acquisition apparatus according to claim 1, wherein the processor is further configured to:
perform image processing according to the mammary gland amount on at least one of the two radiographic images or another radiographic image obtained from the two radiographic images.

10. The mammary gland amount acquisition apparatus according to claim 1, wherein the processor is further configured to:
generate an index indicating a possibility of disease occurrence according to the mammary gland amount.

11. The mammary gland amount acquisition apparatus according to claim 1,
wherein an exposure dose to the breast at a time of acquiring a radiographic image having a higher energy distribution between the two radiographic images is smaller than an exposure dose to the breast at a time of acquiring a radiographic image having a lower energy distribution.

12. The mammary gland amount acquisition apparatus according to claim 1,
wherein a radiographic image having a higher energy distribution between the two radiographic images is a pre-shot image.

13. The mammary gland amount acquisition apparatus according to claim 1,
wherein a radiographic image having the high energy distribution between the two radiographic images is one of a plurality of projection images acquired by tomosynthesis imaging of the breast.

14. The mammary gland amount acquisition apparatus according to claim 1,
wherein a radiographic image having the high energy distribution between the two radiographic images is a composite image that is generated by combining a plurality of tomographic images which are reconstructed from a plurality of projection images acquired by tomosynthesis imaging of the breast.

15. A mammary gland amount acquisition method, comprising:
acquiring two radiographic images acquired by radiations transmitted through a breast, wherein the two radiographic images have different energy distributions;
acquiring a first thickness of the breast using one of the radio graphic images;
acquiring a fat absorption coefficient using the first thickness and a first relationship between thickness of breast and fat absorption coefficient;
acquiring a mammary gland absorption coefficient using the first thickness and a second relationship between thickness of breast and mammary gland absorption coefficient; and acquiring an amount of mammary gland contained in the breast using the two radiographic images, the fat absorption coefficient, the mammary gland absorption coefficient, and a tube voltage at a time of imaging the two radiographic images.

16. A non-transitory computer readable recording medium storing a mammary gland amount acquisition program causing a computer to execute:

acquiring two radiographic images acquired by radiations transmitted through the breast, wherein the two radiographic images have different energy distributions;

acquiring a first thickness of the breast using one of the radio graphic images;

acquiring a fat absorption coefficient using the first thickness and a first relationship between thickness of breast and fat absorption coefficient;

acquiring a mammary gland absorption coefficient using the first thickness and a second relationship between thickness of breast and mammary gland absorption coefficient; and acquiring an amount of mammary gland contained in the breast using the two radiographic images, the fat absorption coefficient, the mammary gland absorption coefficient, and a tube voltage at a time of imaging the two radiographic images.

* * * * *